United States Patent [19]
Brunson

[11] Patent Number: 6,086,364
[45] Date of Patent: Jul. 11, 2000

[54] FIXATION MECHANISM FOR POST AND TUBE DENTAL APPLIANCE

[75] Inventor: Thayer R. Brunson, Wheatridge, Colo.

[73] Assignee: RMO, Inc., Denver, Colo.

[21] Appl. No.: 09/178,193

[22] Filed: Oct. 23, 1998

Related U.S. Application Data

[60] Provisional application No. 60/063,890, Oct. 24, 1997.
[51] Int. Cl.[7] ................................. A61C 3/00
[52] U.S. Cl. .................. 433/10; 433/11; 433/17; 433/20
[58] Field of Search ................ 433/11, 22, 23, 433/10, 17, 13, 14, 15, 20

[56] References Cited

U.S. PATENT DOCUMENTS

| | | | |
|---|---|---|---|
| 3,438,132 | 4/1969 | Rubin | 433/11 |
| 4,354,834 | 10/1982 | Wilson | 433/11 |
| 4,571,179 | 2/1986 | Balenseifen | 433/22 |
| 4,741,696 | 5/1988 | Cetlin | 433/17 |
| 4,897,035 | 1/1990 | Green | 433/17 |
| 5,399,087 | 3/1995 | Arndt | 433/17 |

Primary Examiner—John J. Wilson
Assistant Examiner—Patrick A. Hilsmier
Attorney, Agent, or Firm—Sheridan Ross P.C.

[57] ABSTRACT

A dental tube and post combination is disclosed, wherein the dental tube and post have, respectively, a mating projection and indentation so that when the mating portions are fitted together, it is unlikely that the tube and post will be inadvertently separated from one another. However, the combined tube and post combination of the present invention can be readily separated by a dental technician using conventional dental tools. Moreover, each of the tube and post portions of the present invention can be used with conventional posts and tubes without compatibility concerns.

22 Claims, 14 Drawing Sheets

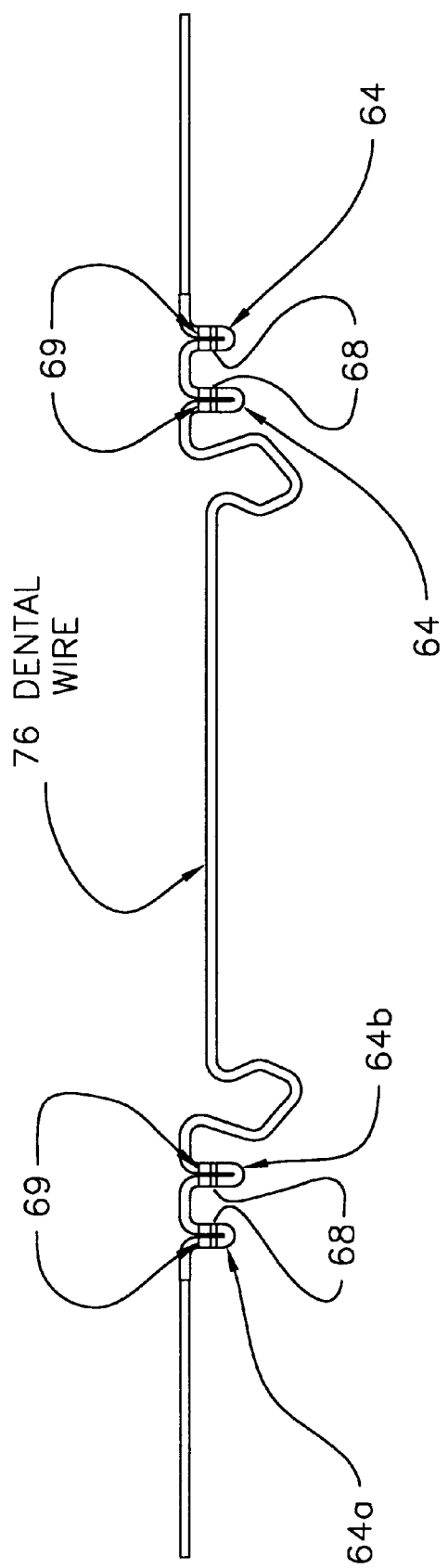

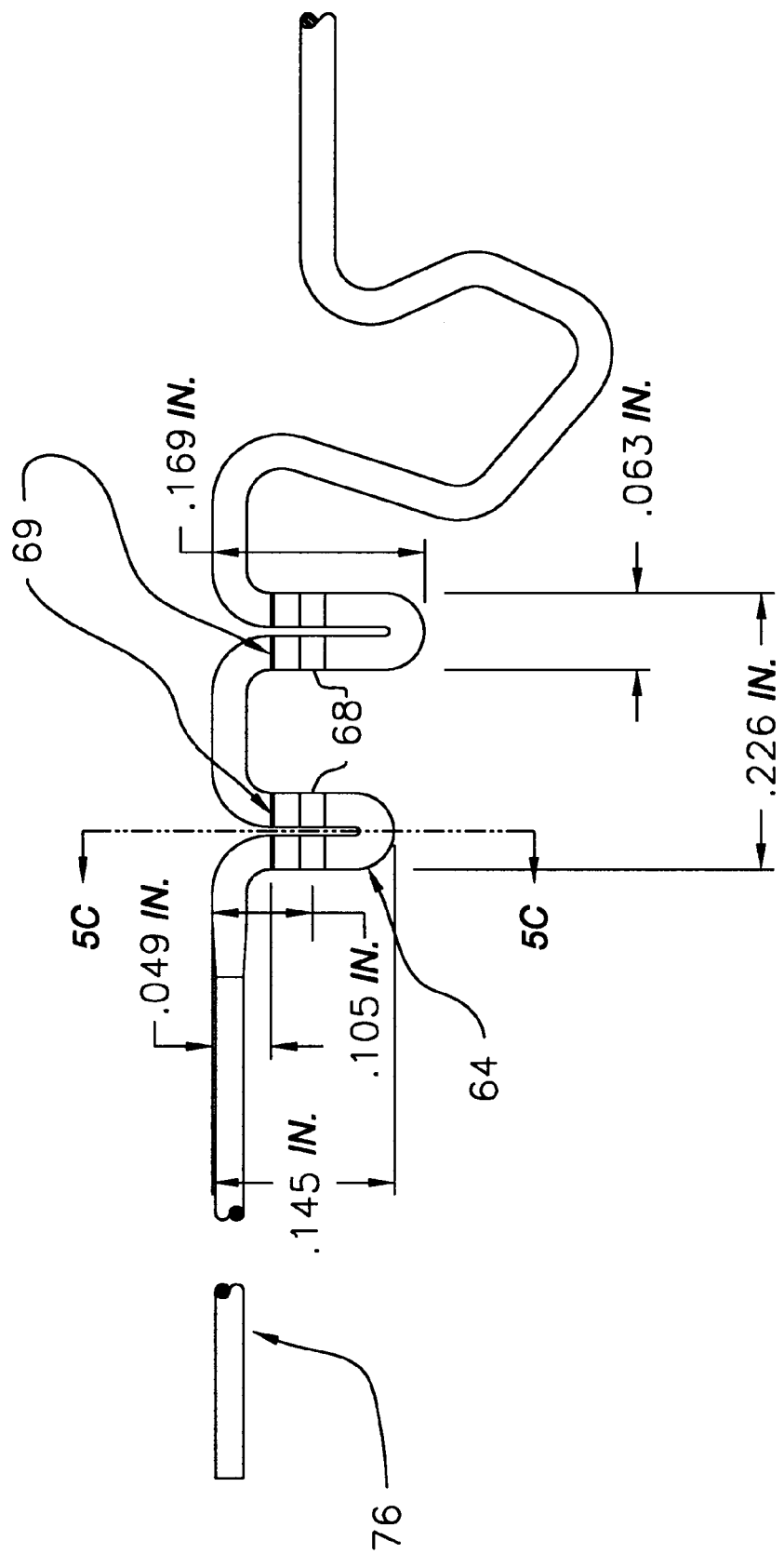

FIXATION MECHANISM FOR POST AND TUBE DENTAL APPLIANCE

This application claims priority from U.S. Provisional Patent Application No. 60/063,890, filed on Oct. 24, 1997.

FIELD OF THE INVENTION

The present invention relates to the securing of a dental post within a dental tube, and in particular, to providing mating projections and indentations that are easily provided using current tube and post manufacturing techniques and machinery.

BACKGROUND OF THE INVENTION

Various configurations of dental appliance tubes and posts have been utilized in orthodontics. When installed in a dental patient's mouth, such mating tubes and posts are typically either frictionally maintained together or secured by ligatures so that a post cannot inadvertently become dislodged from its corresponding tube. It is not uncommon, however, for a dental appliance to have a post which becomes dislodged from the corresponding tube that has been secured to the dental patient's teeth. Moreover, such dislodging can be uncomfortable for the dental patient and in some circumstances may cause injury. For example, if such an orthodontic appliance secured by a tube and post becomes dislodged, the dental appliance may bruise the surrounding tissue when it becomes misaligned. Further, if such misalignment happens, for example, at night, the dental patient's orthodontist may be required to resecure the dental appliance at an inconvenient time.

Orthodontic devices secured by ligatures as well as tubes and posts can similarly become dislodged due to, for example, a ligature that fails. Further, orthodontic appliances using ligatures add additional complexity to the installation, maintenance and removal of the orthodontic appliance.

Moreover, substantially any dental patient perceived play or movement of an installed dental appliance may provoke the dental patient to use their tongue to induce such movements. In many cases such induced movements cause the dental appliance to fatigue and ultimately break. Thus, maintaining proper alignment of dental tubes and posts can be problematic even if the dental tubes and posts do not separate, but merely slip with respect to one another.

Accordingly, it would be advantageous to have a tube and post configuration wherein the post can be seated within the tube in a manner so that it is highly unlikely that the post inadvertently slips within or becomes dislodged from its tube. It would be advantageous if, with proper tools, an orthodontist could straightforwardly remove a post of a dental appliance from its mating tube whenever desirable. It would be advantageous to have a novel tube which could be used together with a conventional post. It would be advantageous to have a novel post which could be used together with a conventional tube. It would be advantageous if the novel tube and post could be manufactured using conventional manufacturing equipment and techniques presently employed to manufacture conventional tubes and posts.

SUMMARY OF THE INVENTION

In accordance with the present invention, a novel tube and post configuration is provided for fixedly securing a post within a tube, while allowing the post to be removed when desired. In one embodiment, the tube of the present invention includes an inwardly directed portion of the tube wall that projects into the post insert passageway of the tube for engaging the post and thereby firmly securing the post within the tube against inadvertent dislodgment. The inward projection of the wall of the tube into the passageway can be in the form of a spring-like "detent" that is capable of limited inward or outward flexing according to the contour of a post that is inserted into the tube. Furthermore, the post of the present invention includes an indentation for mating with the detent of the tube wall. Thus, when the post is fully inserted into the corresponding tube, the post indentation mates with the tube detent for securing the post within the tube.

The mating of the novel tube and post of the present invention also provides for the extraction of the post from the tube given an application of an appropriate amount of force in an appropriate direction. In particular, the present tube and post can be decoupled by using conventional dental equipment by prying the dental post from its tube. Furthermore, it is important to note that such decoupling preferably does not unseat dental band cement, fracture the tube or exceed a dental patient's comfort level.

The mating of the tube and post of the present invention is intended to stabilize and provide additional rigidity against unintended movement to an installed dental appliance. Thus, by mating the post indentation and the tube detent in a manner wherein substantially simultaneously with such mating, a post insertion stop is also contacted, the seating of the post and tube is further enhanced, thus contributing to the overall rigidity of the installed dental appliance. Moreover, when a pair of tube and post combinations of the present invention are installed in a spaced apart fashion, even further rigidity can be obtained. That is, typically the posts will be attached to a common dental appliance so that this spaced apart seating of the tube and post pair reduces any tendency for a pivoting motion to arise at any single one of the tube and post combinations.

While not wishing to be bound by any theory, it is believed that the rigidity resulting from the use of an adjacent pair of tube and post combinations is more than twice as great as a single tube and post. It is believed that this synergistic result is due to a "moment of resistance" which is created by the spaced apart relationship of the adjacent pair of tube and post combinations.

The dental tube and post of the present invention can also be provided in a number of different embodiments. For example, the inwardly directed projection of the tube can be provided by a detent impressed within the wall of the tube, or by dimples or indents also impressed within a wall of the tube. Further, such inwardly directed projections can have various configurations having various inwardly directed peaks and/or ridges that serve to catch on the indentation of the post when inserted into the tube. Such inwardly directed projections can optionally be at various angles to assure proper alignment of a dental appliance when mated with corresponding angled indentations on dental posts of the present invention. Thus, for dental appliances having a plurality of tube and post combinations, differently angled mating tube detents and corresponding post indentations may be used to secure the dental appliance effectively so that there is no perceived movement by the dental patient.

Moreover, it is an aspect of the present invention that the novel tube can also be utilized with conventional posts that do not have mating indentations. Accordingly, when such a conventional post is used, the inwardly projecting portion of the tube serves to enhance the friction for securing the post within the tube.

Additionally, it is an aspect of the present invention that a post according to the present invention can also be utilized with a conventional tube. Thus, conventional tubes and posts can be mixed and matched with the tubes and posts of the present invention so that there can be an easy transition between the use of orthodontic appliances having conventional tube and post securing means and the use of the tubes and posts of the present invention.

Embodiments of the present invention can be such that the tube and post can be inserted into one another in a "vertical" orientation, wherein the post is inserted into a tube along an axis substantially parallel with the longitudinal or apical axis of the dental patient's teeth. Alternatively, in other embodiments, the novel tube and post of the present invention can be oriented parallel to the occlusal plane of the dental patient's teeth in a "horizontal" orientation.

It is an aspect of the present invention that the novel dental post can be made from dental wire that is appropriately configured, or from flat metal (such as a stainless steel ribbon) from which the novel post may be stamped.

The novel tube and post of the present invention can be manufactured using substantially the same machines and machining techniques that are utilized in manufacturing conventional tubes and posts. Therefore, there is substantially no retooling involved in manufacturing the tubes and posts of the present invention.

Because the tube detent is manufactured in a manner so that the tube is not fractured or punctured, the tube retains substantially all the strength of a tube without the detent.

It is an aspect of the present invention that no additional training is required by orthodontists and their technicians with regard to installation and removal of the orthodontic appliances utilizing the present invention. Thus, the present invention may be characterized as retroactively compatible with current orthodontic appliances, current orthodontic manufacturing procedures, and current skill levels for orthodontists and technicians.

Additional features and aspects of the present invention will become evident from the detailed description and the accompanying figures provided herein.

BRIEF DESCRIPTION OF THE DRAWINGS

FIG. 5A shows a dental wire 76 having posts 64 according to the present invention.

FIGS. 5B and 5C provide alternative views and additional detail regarding the posts 64 of the dental wire 76 of FIG. 5A.

DETAILED DESCRIPTION OF THE PREFERRED EMBODIMENT

Figure 1:
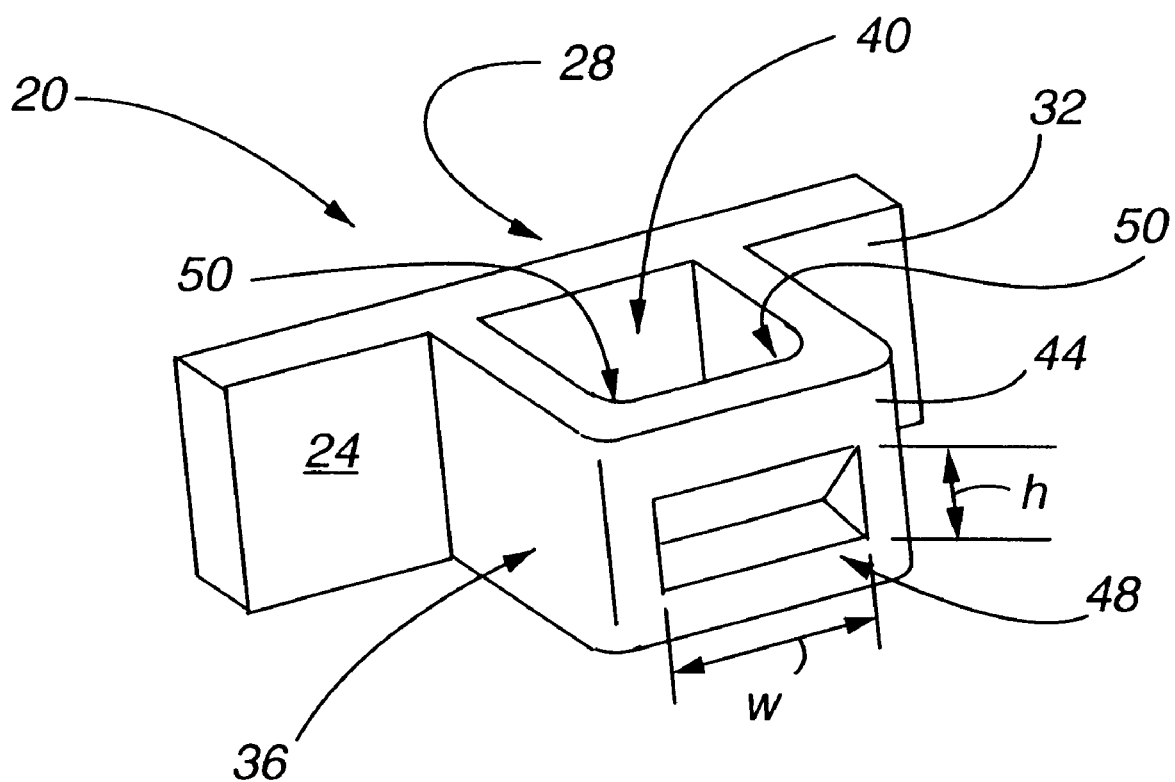
FIG. 1 is a perspective view of an embodiment of a tube according to the present invention. This embodiment preferably is utilized for securing a mating post in a vertical orientation as defined in the summary above.

In FIG. 1, an embodiment of an orthodontic dental appliance tube 20 according to the present invention is shown. The tube appliance 20 includes a base portion 24 whose occluded side 28 attaches to, for example, a band placed around one of a dental patient's teeth. Attached to the front side 32 of the base portion 24 is a dental tube 36 (or more generally, a sheath) having a post insert passageway 40 therethrough. Formed into the wall 44 of the dental tube 36 is a detent 48 that projects inwardly into the post insert passageway 40. The detent 48 has been exaggerated in the present figure for illustration. In one embodiment, the detent 48 has a width, w, that is in one embodiment preferably 70% to 85% of the width of the post insert passageway 40. Further, the detent 48 is centered on the wall 44 so that there are sufficient non-detent areas between the portion of the detent projecting into the passageway 40 (this portion being shown in FIG. 2 as the interior portion 60) and the passageway corners 50 so that the detent can appropriately flex with the insertion of a dental post. Alternatively, note that the non-detent areas can have a distance between the detent and the passageway corners 50 approximately equal to a height, h, of the detent. Additionally, note that the height, h, of the detent 48 is such that the ratio of w to h is approximately 5:1 or greater. Moreover, the detent 48 protrudes into the post insert passageway 40 with dimensions substantially corresponding to the external dimensions of the detent 48. Thus, the interior portion 60 has a width of approximately w and a height of approximately h. Furthermore, note that h is preferably in the range of 0.165 inches to 0.026 inches. Additionally, the depth that the interior portion 60 extends into the post insert passageway 40 is preferably 0.001 to 0.003 inches, with approximately 0.002 inches being most preferable. Also note that the dimensions w and h as discussed hereinabove are more accurately represented in FIGS. 4 and 6. As shown particularly in FIG. 2, the detent 48 is angled so that a dental post being inserted in the direction of arrow 52 slidably contacts the interior portion 60 of the detent 48 projecting into the interior of the passageway 40 for insuring a snug fit of the dental post. Further, the detent 48 is proportioned so as to act in a spring-like fashion upon encountering a dental post in that when a dental post is urged into contact with the interior portion 60, in the passageway 40, the detent is capable of flexing and returning generally in the directions of double-headed arrow 56 as the interior portion 60 follows a contour of a dental post being inserted.

Figure 2:
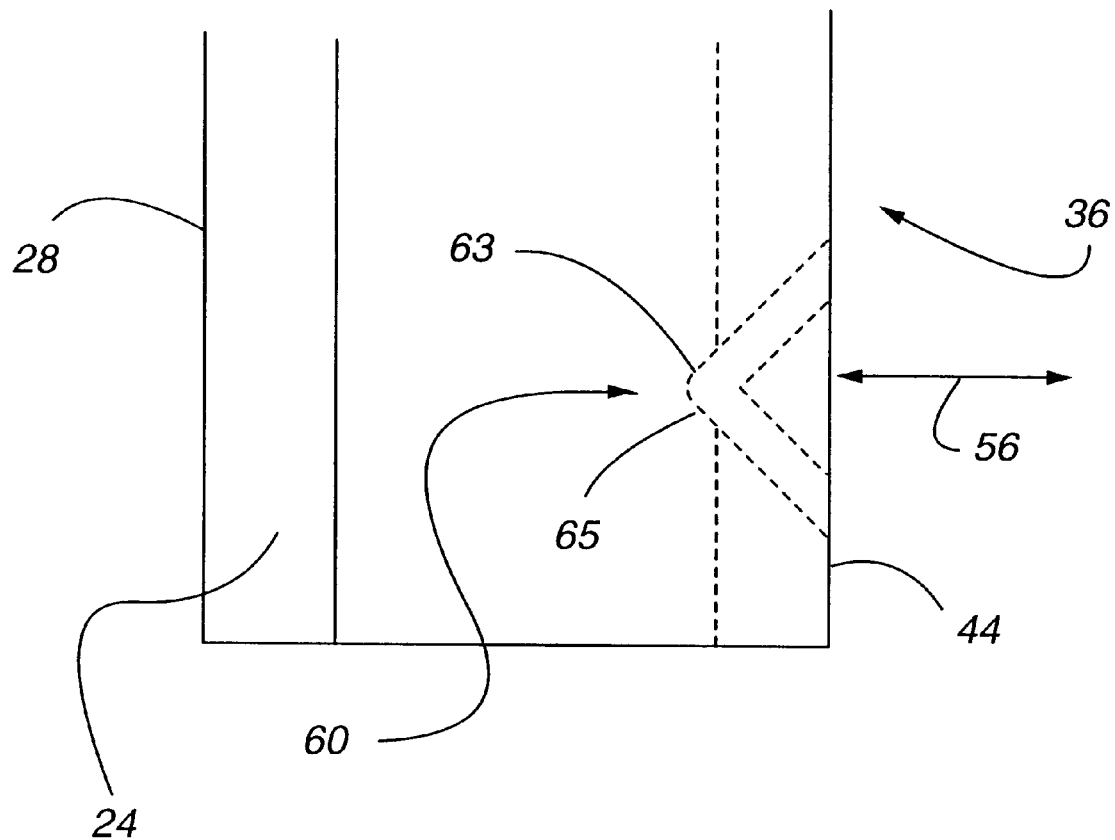
FIG. 2 is a side view of the tube appliance 20 of the present invention shown in FIG. 1.

The interior portion 60 of the detent can have other contours different from the symmetrical "V" in FIG. 2. In particular, the contour can be racket-like in that the side of the interior portion 60 that initially contacts an inserted dental post 64 (e.g., side 63) has a gradual slope and the opposite side (e.g., side 65) abruptly falls away.

Moreover, due to the configuration and dimensions of the detent 48, a conventional dental post that is intended for insertion into a conventional tube appliance is also capable of being inserted and secured within the tube appliance 20 of the present invention. Moreover, the tube appliance 20 more firmly holds such a conventional dental post in position than a conventional tube appliance.

Figure 3:
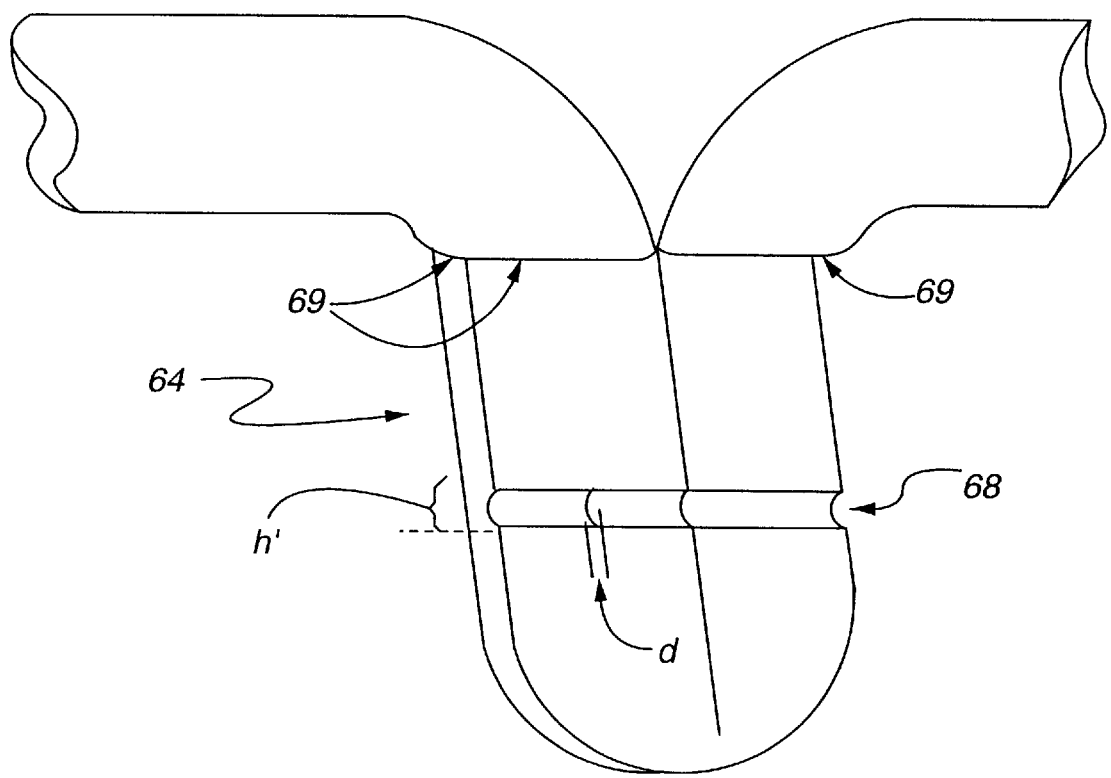
FIG. 3 shows a perspective view of a dental post 64 of the present invention for use with the dental appliance 20 illustrated in FIGS. 1 and 2.

In FIG. 3, a new dental post 64 according to the present invention is illustrated. The dental post 64 includes a novel indentation 68 for mating with the interior portion 60 of the detent 48 when the dental post 64 is inserted into the post insert passageway 40. The indentation 68 is positioned along the dental post 64 so that when the dental post is fully received within the post insert passageway 40, the indentation 68 mates with the interior portion 60 of the detent 48. Note that, in one embodiment, the mating indentation 68 and the interior portion 60 are positioned so that they mate substantially simultaneously with a post stop 69 coming in contact with an end of the tube 36. That is, the post stop 69 is a portion of the post 64 and/or its connection to the dental appliance containing it such that the post stop is sufficiently expanded in size so that it cannot enter the post insert passageway 40. Further note that the present invention provides positive feedback to the orthodontist installing the dental appliance having the novel tube and post. That is, when the detent 48 (i.e., interior portion 60) engages the indentation 68, a combination is generated of a sufficiently abrupt movement or acceleration of the detent into the indentation and subsequently a sudden stopping when the detent reaches its furthest extent within the indentation. Thus, this combination is detected by the orthodontist, thereby assuring the orthodontist of proper seating of the post into its corresponding tube. Additionally, in one embodiment, the indentation 68 can be slightly offset from the interior portion 60 to which it is to be mated so that when the post stop 69 contacts the tube 36 end, the interior portion 60 is only partially seated within the indentation 68. Thus, due to the resilience of the detent 48, the interior portion 60 exerts a force along the direction of post insertion that causes the post stop 69 to remain in contact with the tube end.

In one embodiment, the indentation extends the entire width of the dental post 64 and has other dimensions substantially identical to those of the detent 48. That is, the depth d of the indentation is preferably in the range of 0.001 to 0.003 inches, and more preferably, approximately 0.002 inches. Additionally, the height h' is preferably in the range of 0.0165 inches to 0.026 inches with a more preferred height of approximately 0.021 inches. Further note that such indentations can have various cross sectional contours in the post insertion direction. In some embodiments, such cross sections can be circular or elliptical with a radius (or equivalent measurement) of approximately 0.018 inches to 0.027 inches. Moreover, it is important to note that such indentations 68 can be formed using conventional post manufacturing techniques and machines.

Additionally, the dimensions of the interior portion 60 and the indentation 68 are such that when the indentation 68 and the interior portion 60 mate, it is very unlikely that the dental post 64 will become dislodged from or allow slippage within the post insert passageway 40 inadvertently such as when a patient wearing the novel combination of tube appliance 20 and dental post 64 is eating or sleeping. However, note that the dental post 64 is capable of being removed from the post insert passageway 40 by exerting a sufficiently welldirected exiting force on the dental post 64. In particular, such force is preferably provided by a conventional dental tool used in examining and/or cleaning a dental patient's teeth (e.g. I-358 band pusher/scaler). Accordingly, the novel tube appliance 20 and dental post 64 combination may be referred to as "fixed/removable" in that once they are mated together fully, they are substantially fixed in place, but can be removed or disengaged from one another by an effectively directed force that is of sufficient strength and direction so as to be unlikely to be inadvertently applied during a dental patient's daily activities. However, such a force can be applied by a dental technician using appropriate dental tools.

Figure 4A:
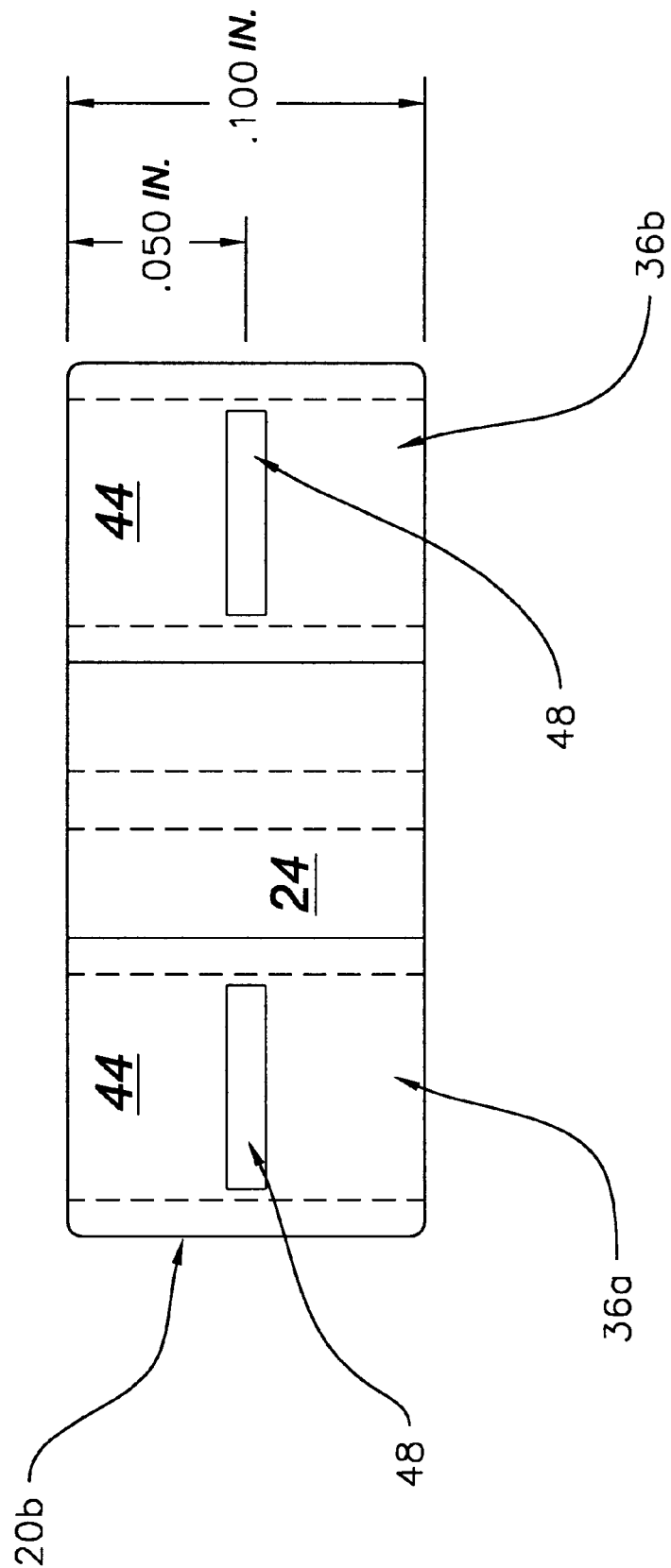
FIGS. 4A and 4B show an alternative embodiment of the tube appliance 20b of the present invention, wherein the appliance has two substantially identical tubes incorporated therein.
Figure 4B:
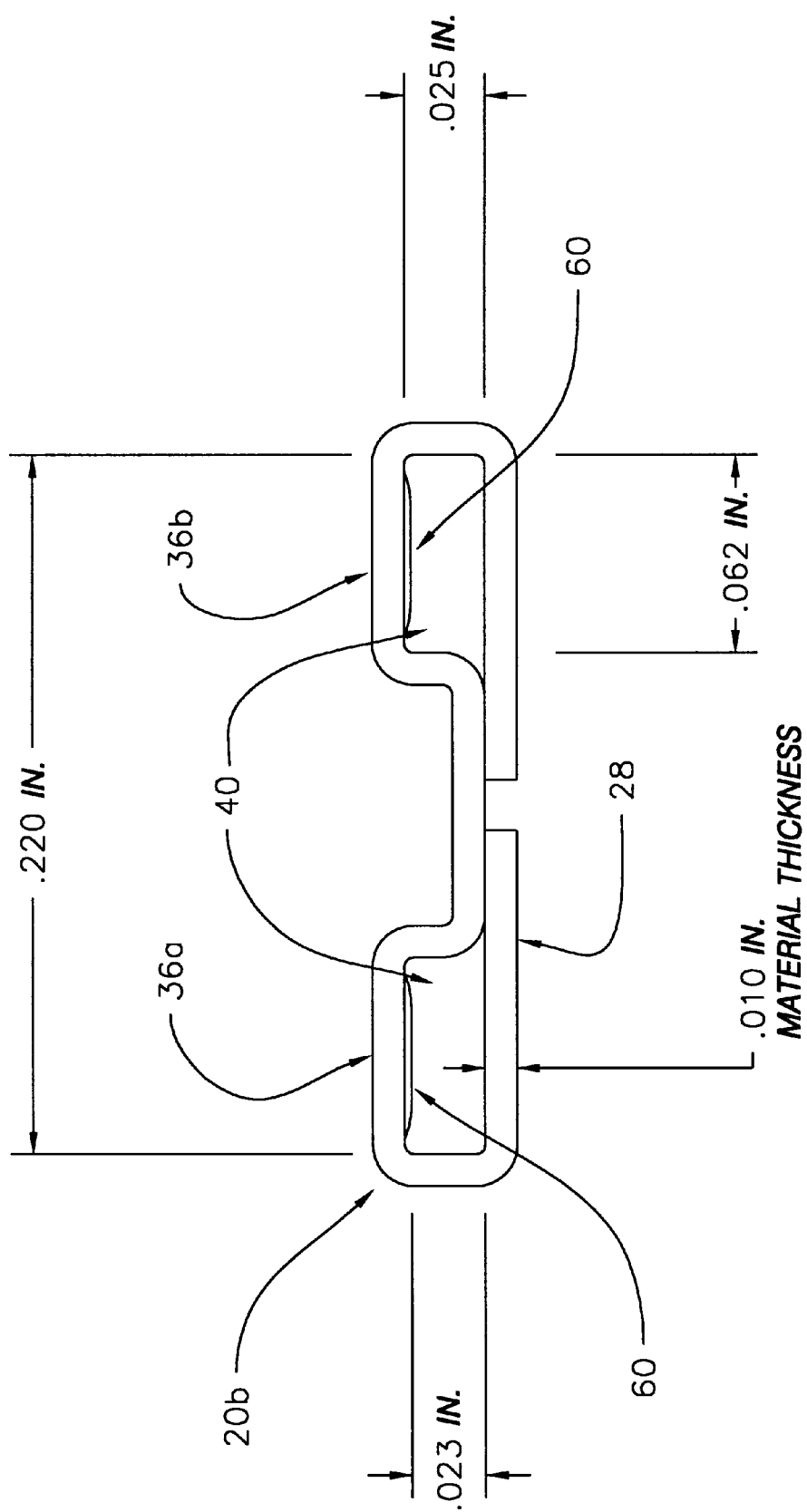

FIGS. 4A and 4B illustrate an alternative embodiment 20b of the tube appliance of the present invention. In particular, the tube appliance 20b of these figures includes twin dental sheaths or tubes 36a and 36b, each having a detent 48 impressed into their respective walls 44. Accordingly, the tube appliance 20b may be utilized with the dental light wire appliance 76 illustrated in FIGS. 5A, 5B and 5C. In particular, note that the dental wire appliance 76 includes two pairs of dental posts 64 (one pair having labels 64a and 64b), wherein each such dental post includes an indentation 68 substantially as described hereinabove for mating with the interior portions 60 of the detents 48 of the tube appliance 20b. For example, once a pair of appropriately positioned tube appliances 20b has been installed within a dental patient's mouth, the dental wire appliance 76 can also be installed so that the dental posts 64a and 64b can be inserted into the dental tubes 36a and 36b, respectively, for one of the tube appliances 20b. Accordingly, the interior portions 60 of the detents 48 mate with the corresponding indentations 68 of the dental posts 64a and 64b, and the post stops 69 may abut the ends of the dental tubes into which the dental posts are inserted.

Figure 6:
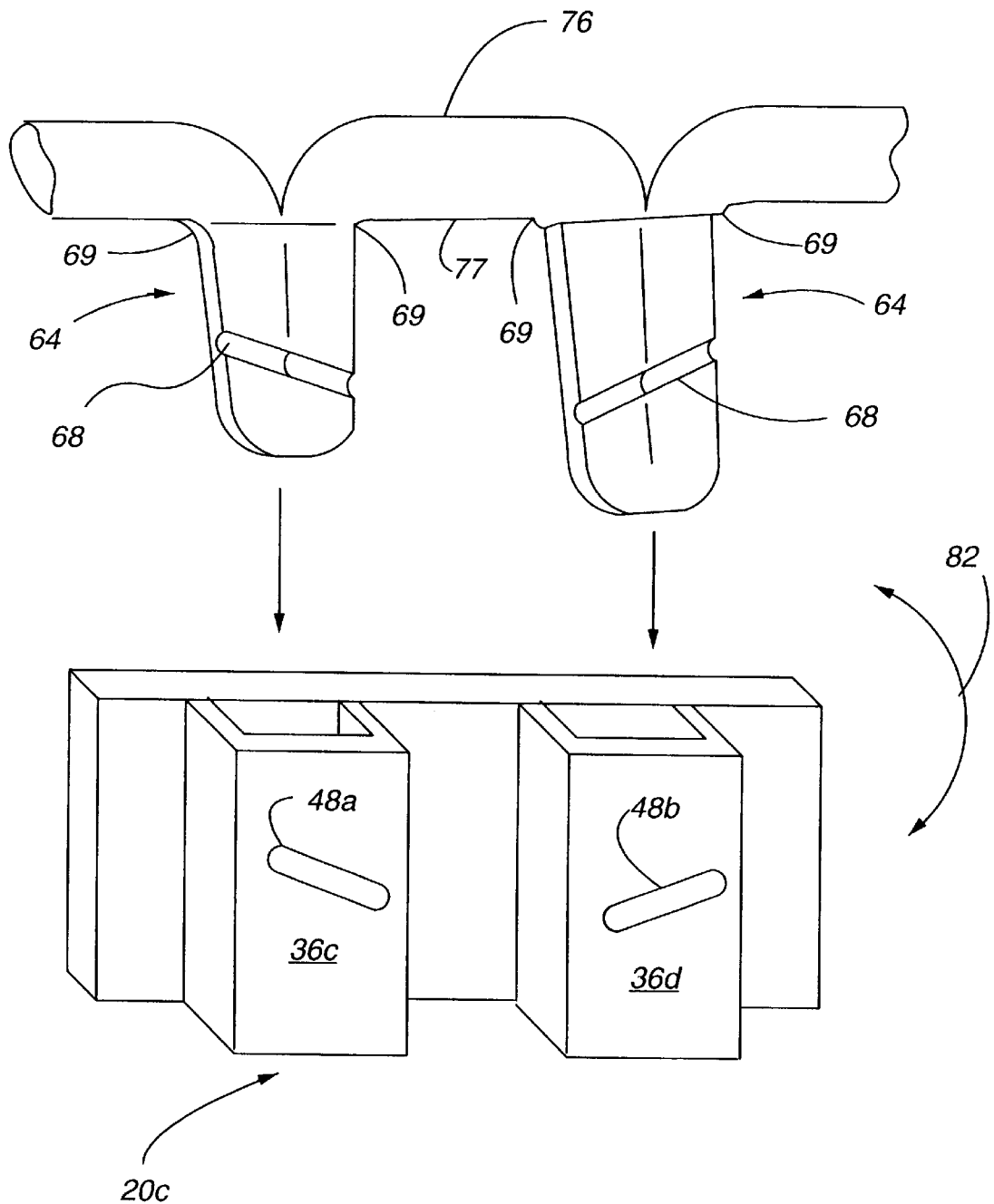
FIG. 6 illustrates an embodiment of a tube appliance 20c and mating dental posts 64, wherein the detents 48a and 48b, and their mating indentations 68 are angled with respect to one another.

FIG. 6 illustrates yet another embodiment of the present invention, wherein the tube appliance 20c includes pairs of dental tubes 36c and 36d and each of these dental tubes includes a detent 48a and 48b. Note that these detents are similar to the detents 48 of the previous figures except that the detents 48a and 48b are angled to one another. Correspondingly, the dental posts 64 of this figure have similarly angled indentations 68 for mating with the detents 48a and 48b. Note that in some cases, the angling of at least one of the detents 48a and 48b may inhibit the dental appliance having the dental posts 68 from being perceived as being loose by the dental patient. That is, the angled mating detents and indentations can contribute to securing an installed dental appliance so any play or rocking between the tubes and the posts in the directions of double headed arrow 82 can be alleviated. Further note that as described in FIG. 3, there are post stops 69 that can also facilitate in securing the dental posts 64 in place. Additionally, the underside 77 of the segment of the dental wire 76 between the two posts may also abut some embodiments of the tube appliance 20c when the tube and post are mated together. Thus, the underside 77 can also serve as a post stop, thereby enhancing the rigidity of the installed wire dental appliance provided by dental wire 76. Also note that the double tube and post configuration such as is represented in the present figure provides considerably greater rigidity and/or stability to the dental appliance provided by the dental wire 76 than would be anticipated. That is, the spacing between the dental tubes yields a moment of resistance that is more than double the moment of resistance of a single tube and post configuration.

Figure 5C:
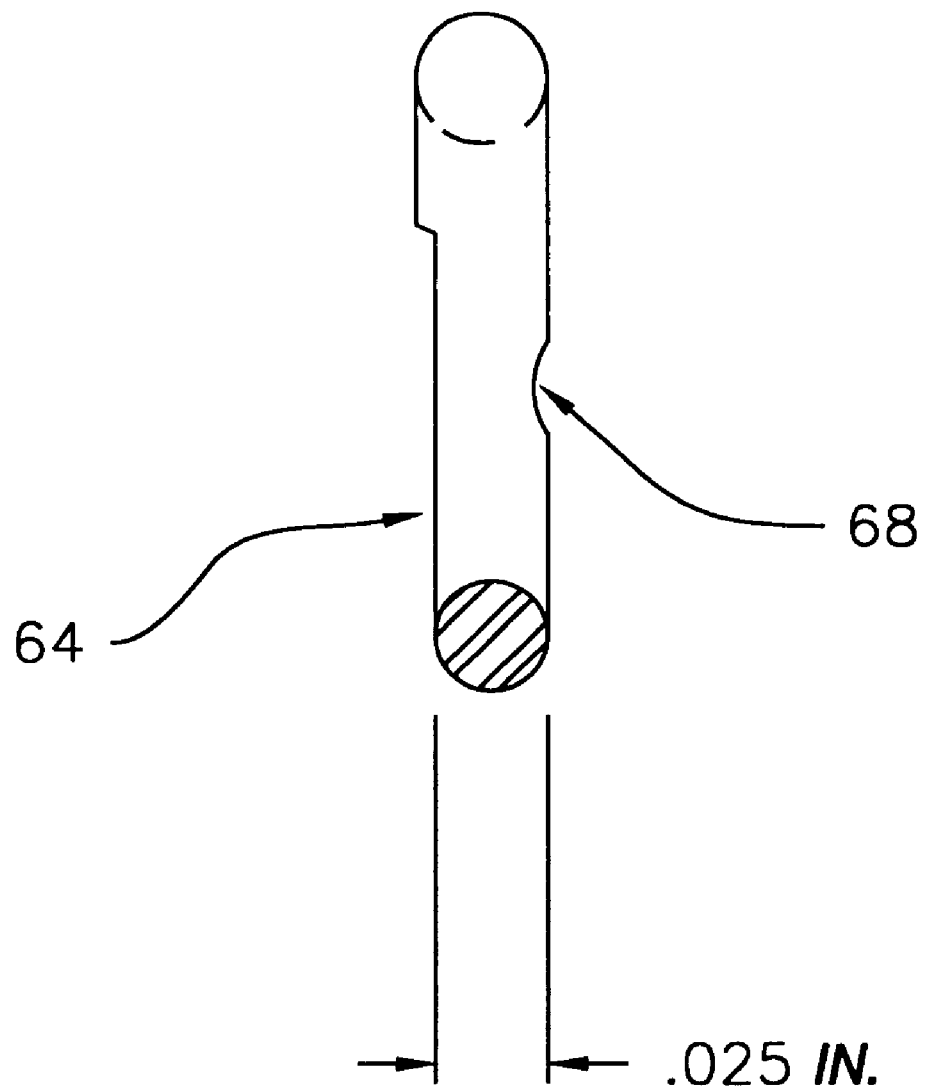
Figure 7A:
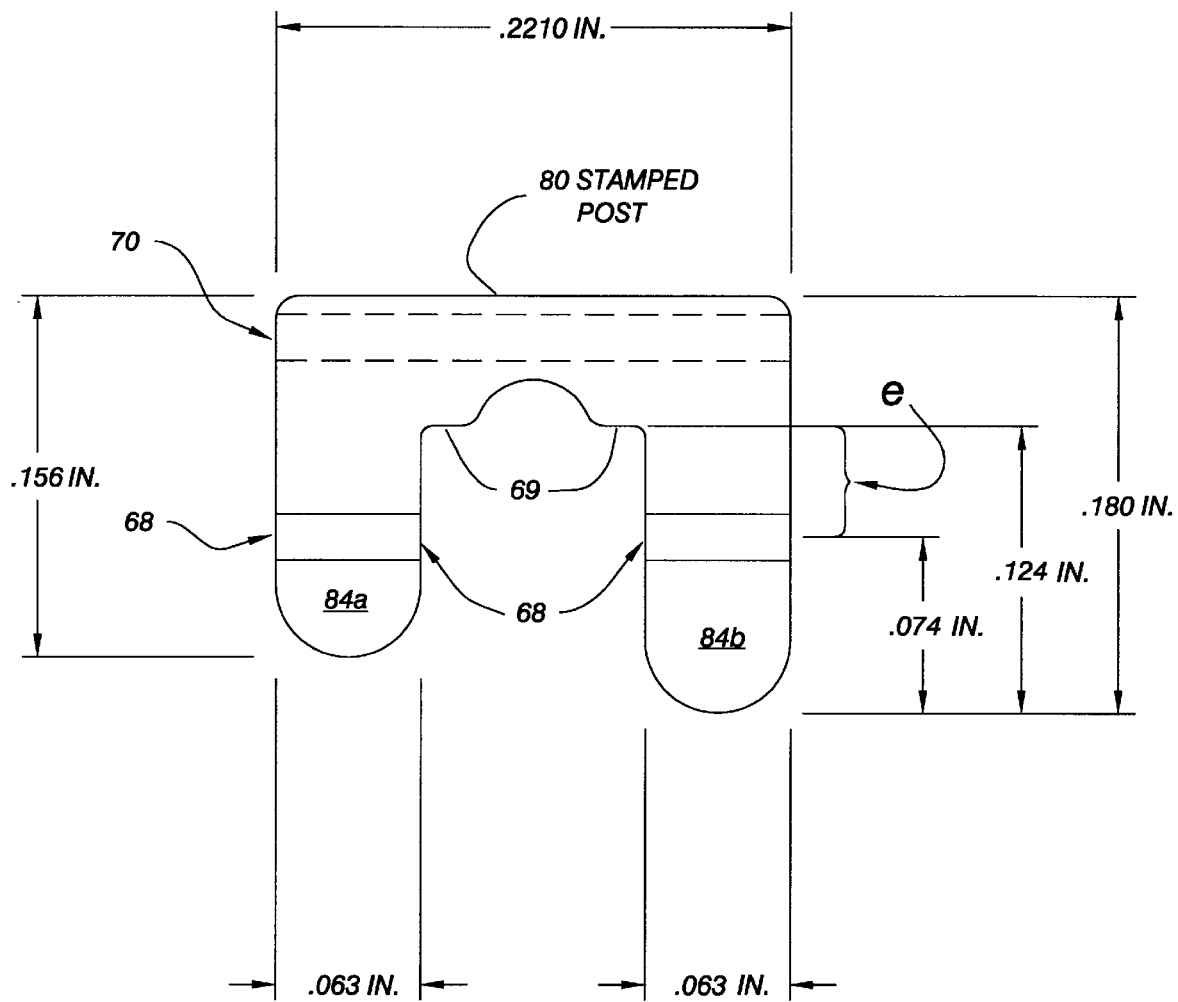
FIGS. 7A and 7B show views of an orthodontic appliance having twin posts according to the present invention, wherein this appliance is stamped from a single piece of flat metal.
Figure 7B:
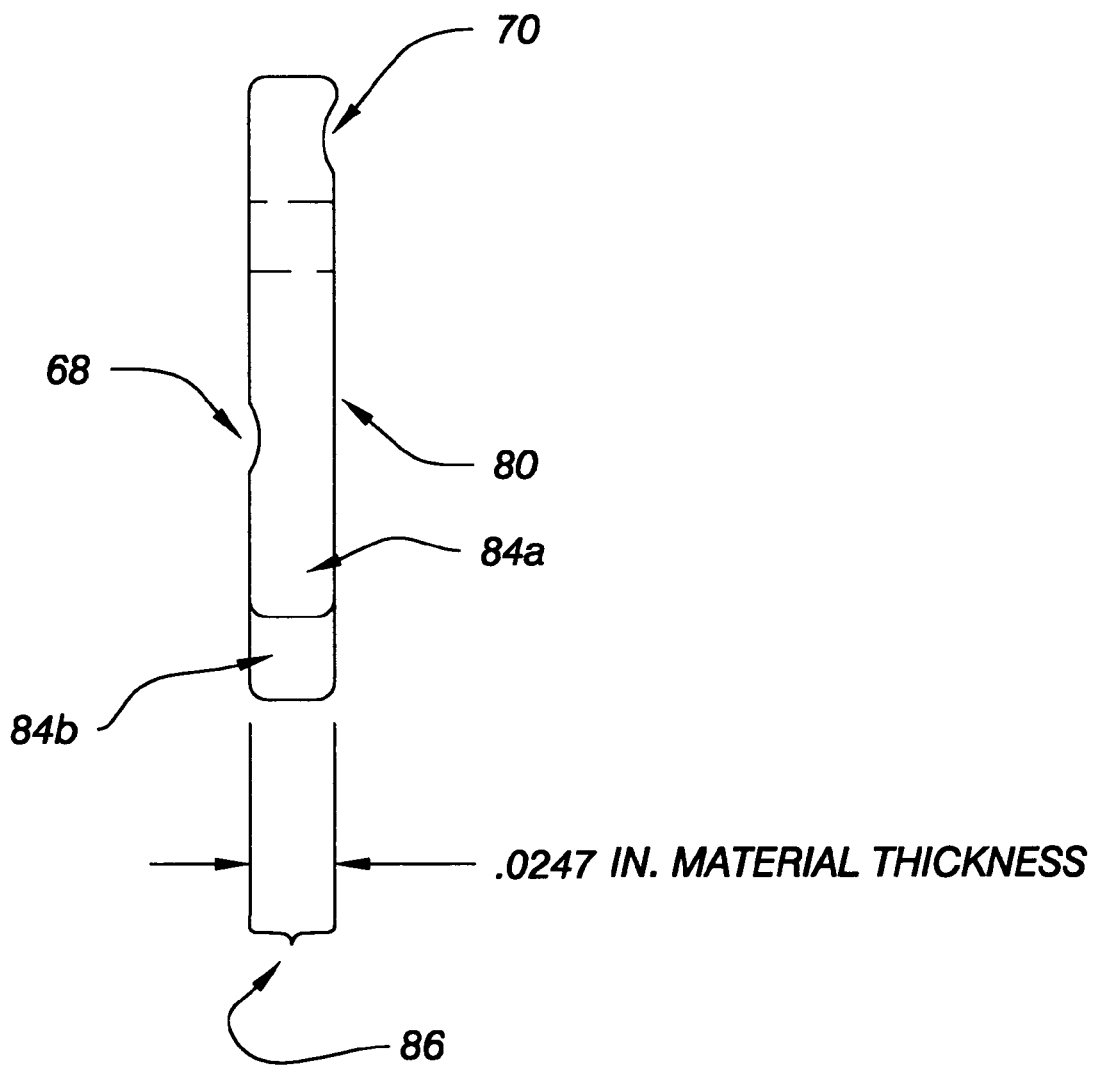

FIGS. 7A and 7B illustrate a stamped post 80 dental appliance that can serve as an alternative for the wire version of the dental posts 64 as shown in FIGS. 5A, 5B and 5C. Accordingly, as the name suggests, the stamped post 80 of FIGS. 6 can be stamped out of a single piece of metal so that dental posts 84a and 84b may be simultaneously provided into the dental tubes 36a and 36b such that the indentations 68 on these posts align with the interior portions 60 of the detents 48 of the dental tubes 36a and 36b. It is important to note that as with the embodiment of FIG. 3, post stops 69 are provided, these post stops providing all the functionality discussed hereinabove in that they provide additional reinforcement for retaining the dental post 64 within its tube. Moreover, note that when manufacturing a stamped dental post 80, the positioning of the stamped post for forming the indentation 68 is likely measured from the post stop 69; i.e., this measurement being distance "e" in FIG. 7A.

Figure 10:
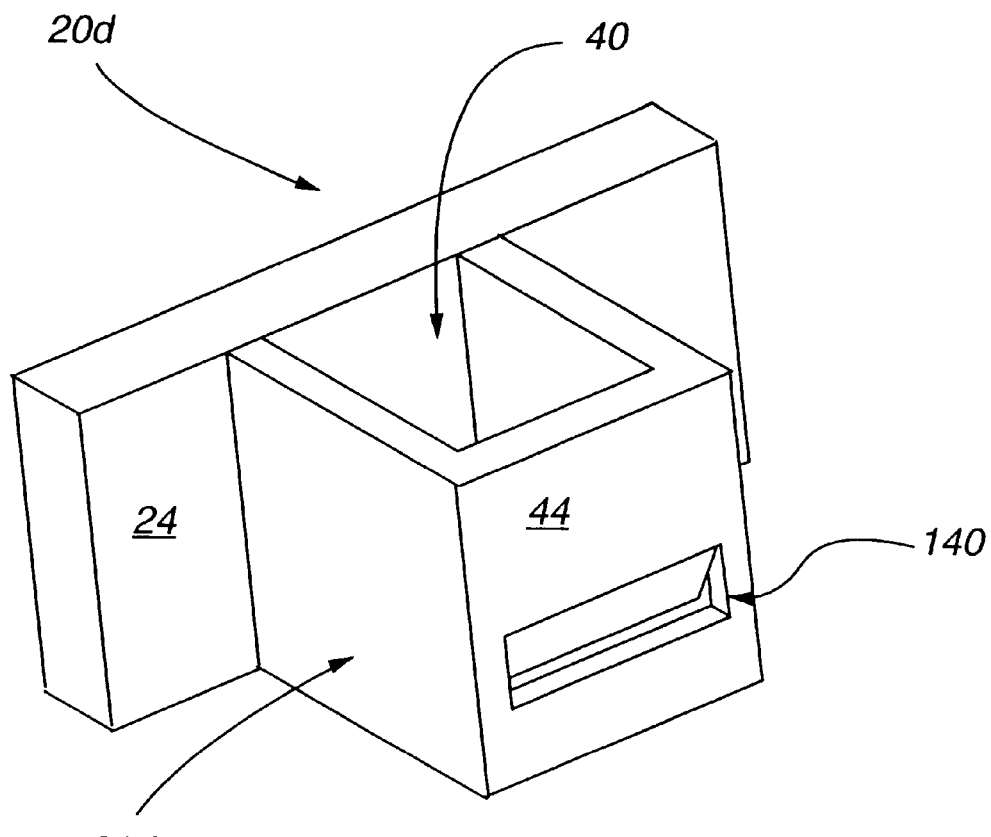
FIGS. 10 and 11 illustrate another alternative embodiment of the dental tube for the present invention, wherein a tang replaces the detent 48.
Figure 11:
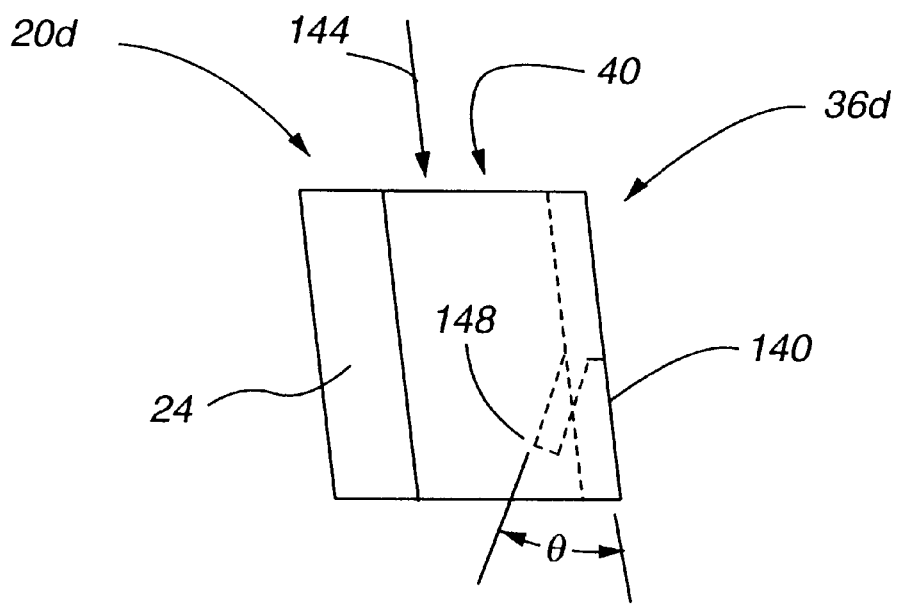

An alternative embodiment for the tube appliance of the present invention is provided in FIGS. 10 and 11, wherein identical components from previously described embodiments have identical numbers in their labels. The tube appliance 20d shown in this figure differs from previous embodiments in that instead of a detent on wall 44, there is a tang 140. The tang 140 is disconnected from the remainder of the wall 44 on three of its sides and projects into the post insert passageway 40 at an angle 0. Accordingly, the tang 140 functions similarly to the embodiment of the detent interior portion 60 described above that has a racket-like contour. That is, given that a dental post is inserted into the post insert passageway 40 in the direction of arrow 144, when the dental post contacts the tang 140, the tang is forced to pivot counterclockwise about its attachment to wall 44 to accommodate the dental post. Assuming the inserted dental post is an embodiment of the present invention, when the edge 148 of the tang enters the indentation of the dental post, the tang 148 has a tendency to spring back to its original angled position and thereby further enter into the indentation for securing the dental post with dental tube 36d.

Note that the stamped post 80 also includes an indentation 70 on the opposite side from the indentation 68, this indentation being for positioning a dental wire therein when welding the stamped post to the dental wire.

It is important to note that both the tube appliance of the present invention and the mating dental post of the present invention can be utilized with conventional dental tubes and posts. That is, as mentioned hereinabove, the tube appliance embodiment 20 can be used with conventional dental posts that do not contain the indentation 68 of, for example, FIGS. 3, 5A, 5B, 5C, 7A and 7B. Further, note that the dental posts 64 illustrated in the these latter figures can also be utilized with conventional tube appliances that do not have a detent 48. Accordingly, the novel tubes and posts of the present invention can be easily phased into a dental practice without abandoning any current stock of corresponding conventional tube appliances and dental posts.

Figure 8:
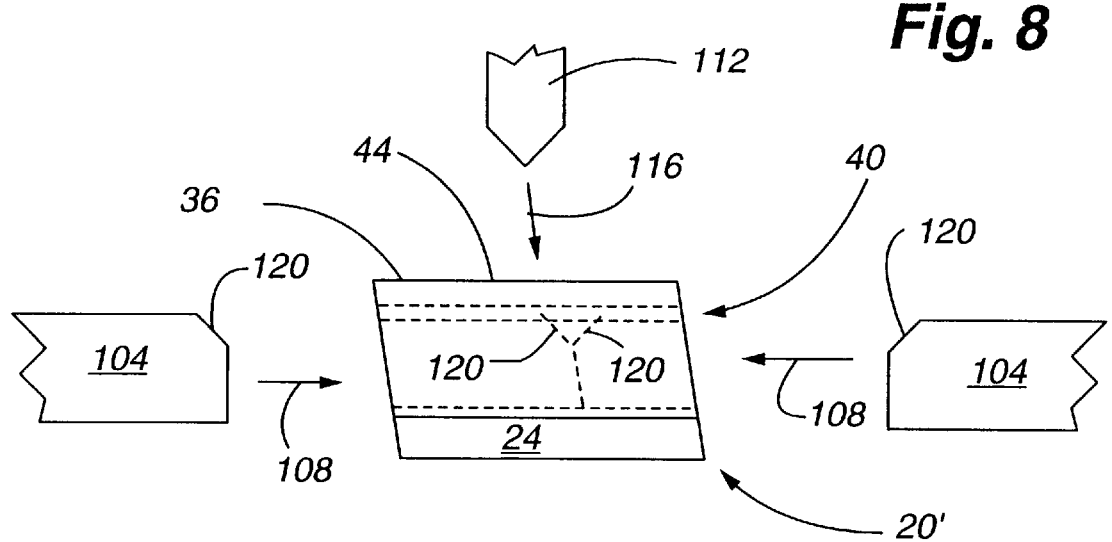
FIG. 8 illustrates the forming of a detent 48 on a dental tube 36 such as the dental tubes 36, 36a and 36b of FIGS. 1 and 4.

Various manufacturing processes for the present invention will now be discussed. Regarding the novel tube appliances 20 and 20b, reference is made to FIG. 8. This figure shows a tube appliance 20' that has been formed in a conventional manner without the detent 48. Additionally, this figure shows an additional manufacturing step for transforming tube appliance 20' into tube appliance 20. That is, once the tube appliance 20' is appropriately secured in a predetermined position, tube inserts 104 enter the opposing ends of the tube or sheath 36 (as indicated by arrows 108) in a manner so that the opposing tube inserts abut at a predetermined location within the tube 36. Accordingly, the abutting of the tube inserts 108 is indicated by the dashed lines of the tube inserts within the tube 36. Subsequently, a detent impressing die 112 is pressed into the wall 44 along arrow 116 with sufficient force to form a detent 48. Note that the shape and depth of the detent are accurately determined by the configurations of the die 112 contacting the tube 36 and the configurations of the chamfers 120 of the tube inserts 104. Thus, the resulting detent will not crease the tube 36 beyond its intended extent and the tube 36 will not be cracked or punctured. Further, note that to obtain the tube appliance 20b of FIG. 4, a pair of tube inserts 104 and detent impressing dies 112 may be used for creating the detents 48 on the tubes 36a and 36b substantially simultaneously.

Figure 5D:
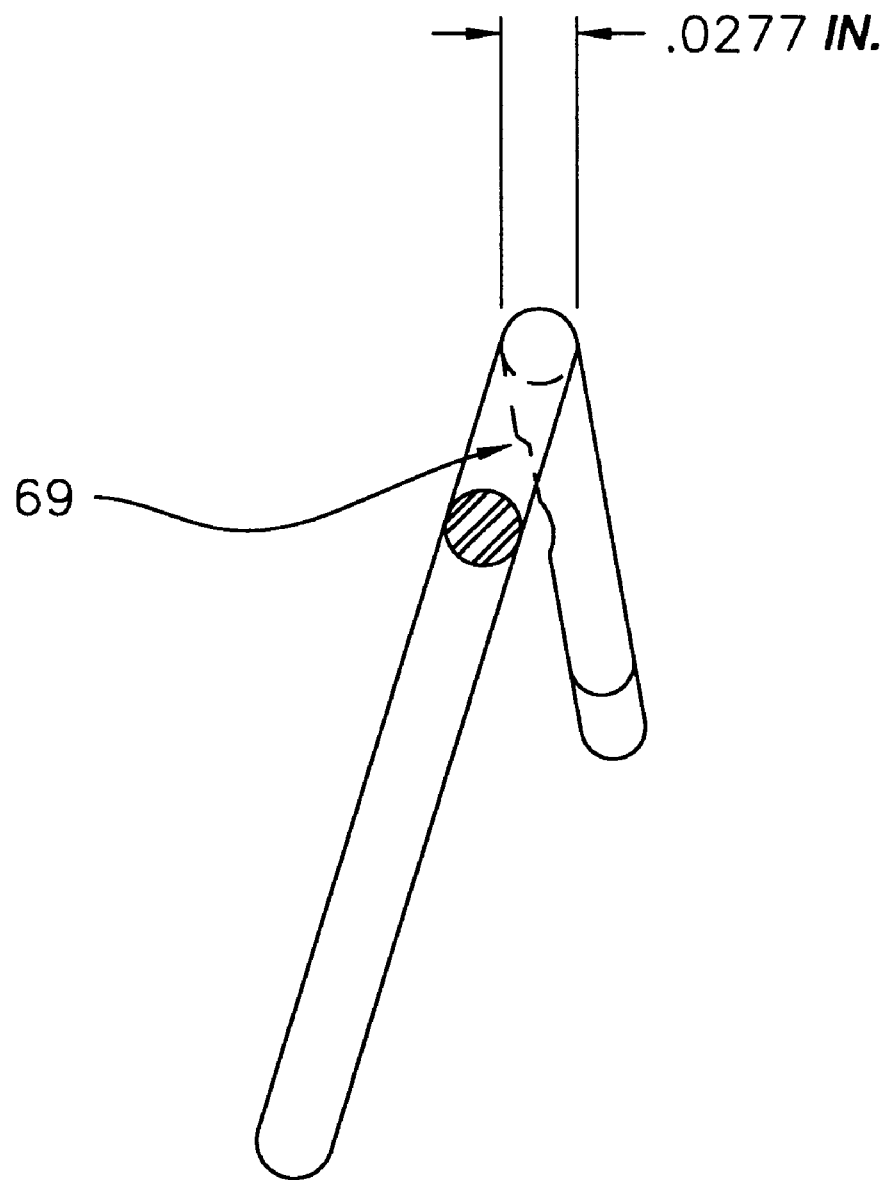
FIG. 5D shows a left end view of the dental wire 76 of FIG. 5B.
Figure 9:
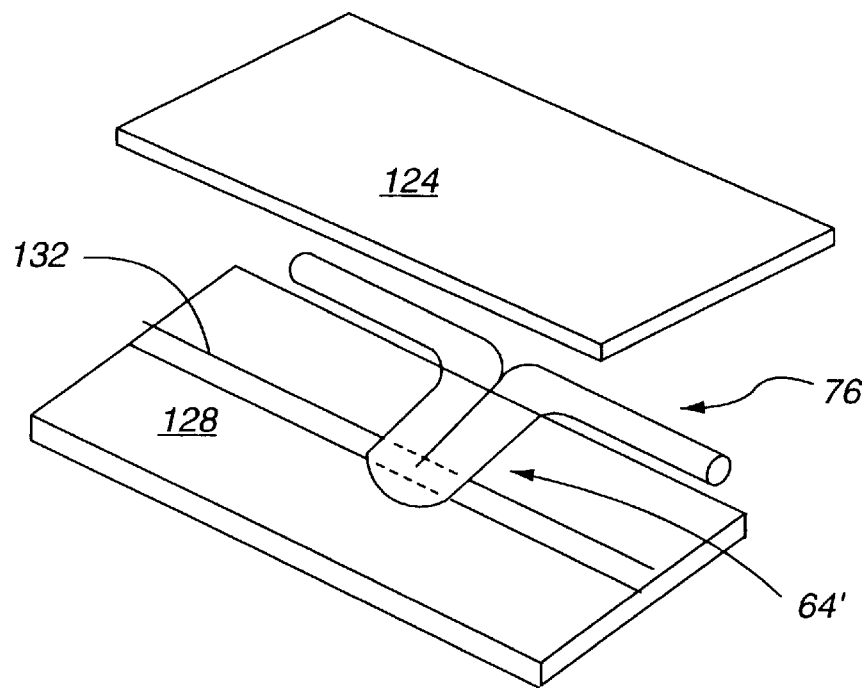
FIG. 9 illustrates the forming of an indentation 68 on a dental post 64.

Regarding the manufacturing of the wire dental post 64 of FIG. 3 and the post 64 of FIGS. 5, reference is made to FIG. 9. This figure shows the dental wire 76 bent to form dental posts 64', wherein the dental post 64' is positioned between two press plates, namely a top platen 124 and bottom platen 128. Accordingly, when the platens are forcefully brought together for "spanking" the dental post 64', this post becomes substantially flat. However, since the dental post 64' is positioned so that a ridge 132 provided on the bottom platen 128 traverses a width of the post, when the post 64' is spanked, indentation 68 is provided along with the flattening of the post 64' to thereby produce the dental post 64.

Regarding the manufacturing of the stamped post 80, 300 series stainless steel flat plate slightly thicker than the 0.0243 to 0.0247 inch thickness desired for the stamped post is provided to a punch press for punching out post pieces having the contour of the stamped post 80. Subsequently, the post pieces are positioned within a press similar to that illustrated in FIG. 8 for spanking so that the thickness of the post pieces is reduced to the thickness 86 (FIG. 7B) of the stamped post 80. Moreover, both the bottom and top platens used to spank the post pieces have ridges similar to the ridge 132 of FIG. 8; i.e., one such ridge is positioned substantially as the ridge 132 is in FIG. 8, and the other ridge is positioned on a bottom surface of the top platen for impressing into the post piece the top groove 70 of the stamped post 80. Thus, when the two platens for the stamped post are brought together with a post piece properly positioned therebetween, a stamped post 80 is subsequently produced.

The foregoing discussion of the invention has been presented for purposes of illustration and description. Further, the description is not intended to limit the invention to the form disclosed herein. Consequently, variation and modification commensurate with the above teachings, and within the skill and knowledge of the relevant art, are within the scope of the present invention. The embodiment described hereinabove is further intended to explain the best mode presently known of practicing the invention and to enable others skilled in the art to utilize the invention as such, or in other embodiments, and with the various modifications required by their particular application or uses of the invention. It is intended that the appended claims be construed to include alternative embodiments to the extent permitted by the prior art.

What is claimed is:

1. An apparatus for releasably securing a dental appliance, comprising:

(a) a dental post having a post length and a post width and an indentation with a first extent substantially traversing said post width, and a second extent in a direction of said post length, wherein a given ratio of said first extent to said second extent is approximately 5 to 1 or greater;

(b) a dental post receiving means for receiving said dental post, said dental post receiving means having a post retaining sheath with an interior for receiving said dental post, wherein when said post is inserted in a direction substantially traverse to said post width into said interior, said interior effectively frictionally engages said dental post;

wherein said dental post receiving means includes one or more projections into said interior for mating with said indentation, wherein said projections engage said indentation at least at points substantially at said post width apart, and said projections are included in an area of said dental post receiving means, wherein said area has extents in a same ratio as said given ratio.

2. An apparatus, as claimed in claim 1, wherein said projections include a first projection having: (a) a first projection extent substantially traversing an entire wall of said interior, and (b) a second projection extent substantially traverse to said first projection extent, wherein a ratio of said first projection extent to said second projection extent is approximately 5:1 or greater.

3. An apparatus, as claimed in claim 1, wherein at least one of said projections is a detent formed on said sheath as an image of a detent forming tool has pressed against an outer surface of said retaining sheath while said interior is supported with a tool for limiting an extent of a detent thereby formed.

4. An apparatus, as claimed in claim 1, wherein at least one of said projections flexes in and out against said dental post.

5. An apparatus, as claimed in claim 1, wherein said dental post is capable of being removed from said interior using conventional dental tools.

6. An apparatus, as claimed in claim 1, wherein said sheath is capable of receiving a conventional dental post not having said indentation.

7. An apparatus, as claimed in claim 1, wherein said dental post is capable of being inserted into a conventional dental tube not having said projection.

8. An apparatus as claimed in claim 1, further including a second dental post and a second dental post receiving means for receiving said second dental post, wherein said dental post receiving means and said second dental post receiving means are spaced apart by a distance, said dental post and said second dental post are also spaced apart by said distance on a dental appliance to which said dental post and said second dental post are attached, wherein when said dental post is received in said post receiving means to form a first coupling, and said second dental post is received in said second post receiving means to form a second coupling, said first and second spaced apart couplings have a moment of resistance that is more than double that of the first coupling.

9. An apparatus as claimed in claim 8, wherein said second dental post has a second post length and a second post width and a second indentation with a third extent substantially traversing said second post width, and a fourth extent in a direction of said second post length, wherein a ratio of said third extent to said fourth extent is approximately 5:1 or greater;
said second dental post receiving means having a second post retaining sheath with a second interior for receiving said second dental post, wherein said second dental post is inserted in a direction substantial traverse to said second post width, said second interior having a second interior width which effectively frictionally engages said second dental post;
wherein said second dental post receiving means includes a second projection into said second interior for mating with said second indentation.

10. The apparatus of claim 1, wherein one of the extents of said area is substantially in a second direction coincident with the post width when said dental post is received in said interior, and said one extent of said area extends approximately 70% to 85% of a maximal possible extension of said interior in the second direction.

11. The apparatus of claim 1, wherein at least one of said projections projects into said interior approximately 0.165 inches to 0.026 inches.

12. The apparatus of claim 1, wherein said dental post is provided from a dental wire.

13. The apparatus of claim 1, further including one or more dental post stops for limiting an amount of said dental post, in the post length direction, that enters said interior, wherein at least one of said projections does not fully mate with said indentation when said dental post stop contacts said dental post receiving means.

14. An apparatus for releasably securing a dental appliance, comprising:
    (a) a dental post having a post length and a post width and an indentation extending substantially across the post width;
    (b) a dental post receiving means for receiving said dental post, said dental post receiving means having a post retaining sheath with an interior for receiving said dental post in a first direction substantially traverse to said post width, so that a width of said interior substantially coincides with the post width;
    (c) a projection for projecting into said interior for mating with said indentation, said projection having: (i) a first projection extent substantially traversing said interior width and (ii) a second projection extent in a direction normal to said first projection extent, wherein a ratio of said first projection extent to said second projection extent is approximately 5:1 or greater.

15. The apparatus of Claim 14, wherein said projection has a spring-like resiliency so that there is an abrupt mating of said indentation and projection that is detectable by a person causing the mating.

16. An apparatus for insertion into an interior of a dental tube, comprising:
    a dental post having a length along a lengthwise direction, and a width traversing said lengthwise direction, wherein said dental post is capable of being inserted into the dental tube in said lengthwise direction;
    an indentation substantially traversing said width at a predetermined position along said length, said indentation having a first extent along said width and a second extent traverse to said first extent;
    wherein a ratio of said first extent to said second extent is approximately 5:1 or greater so that: (a) when the dental tube includes a detent projecting into the interior and capable of mating with said indentation substantially along said first extent, then said mating facilitates maintaining said dental post in a desired alignment, and (b) when the dental tube does not include said detent, then said dental post is capable of being retained in said interior as a dental post without said indentation.

17. An apparatus as claimed in Claim 16, wherein said detent has predetermined orthogonal first and second dimensions having a ratio of approximately 5:1 or greater, wherein said first dimension is substantially coextensive with said first extent of said indentation.

18. The apparatus of claim 16, wherein said dental post is provided from a dental wire.

19. An apparatus for receiving a dental post, comprising:
    a dental tube having an interior with at least one opening for insertion of a dental post in a first direction;
    a detent in a wall of said dental tube providing an interior projecting portion of said wall, said detent having a first extent traverse to said first direction and a second extent in said first direction;

wherein a ratio of said first extent to said second extent is approximately 5:1 or greater so that: (a) when the dental post includes an indentation for mating with said detent, then said mating enhances a rigidity of said dental post to remain in a desired alignment, and (b) when the dental post does not include said indentation, then said detent engages the dental post for increasing a friction for retaining the dental post within said dental tube.

20. An apparatus, as claimed in claim 19, wherein when said dental tube having said detent receives the dental post, said detent is capable of mating with an indentation on the dental post, wherein the indentation has predetermined dimensions in a ratio of approximately 5:1 or greater.

21. A method for releasably securing a dental appliance within a dental patient's mouth, comprising:

inserting a dental post into a dental tube, wherein said dental post has a length along a lengthwise direction, a width traversing said lengthwise direction, and an indentation at a predetermined position along said length, said indentation having a first extent traverse to said lengthwise direction and a second extent in said lengthwise direction, and said first extent being in a ratio to said second extent of approximately 5:1 or greater, and wherein said dental tube has a wall providing an interior with at least one opening for insertion of said dental post in said lengthwise direction, said wall having a detent providing an interior projecting portion of said wall;

contacting said dental post and said interior projecting portion, wherein said interior projecting portion flexes so that said dental post is able to move further into said interior;

mating said indentation and said interior projection when they align so that said detent mates with said indentation along substantially an entire length of said first extent.

22. The method of claim 21, wherein upon completion of said mating step, said detent maintains a force against a side of said indentation, wherein said force urges said dental post into said interior.

* * * * *